(12) United States Patent
Mulliken et al.

(10) Patent No.: US 12,099,654 B1
(45) Date of Patent: Sep. 24, 2024

(54) ADAPTATION OF ELECTRONIC CONTENT

(71) Applicant: Apple Inc., Cupertino, CA (US)

(72) Inventors: Grant H. Mulliken, San Jose, CA (US); Srinath Nizampatnam, Sunnyvale, CA (US); Fletcher R. Rothkopf, Los Altos, CA (US); Brian Pasley, Berkeley, CA (US); Izzet B. Yildiz, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/838,441

(22) Filed: Jun. 13, 2022

Related U.S. Application Data

(60) Provisional application No. 63/212,801, filed on Jun. 21, 2021.

(51) Int. Cl.
  G06F 3/01 (2006.01)
  A61M 21/02 (2006.01)
  A61M 21/00 (2006.01)

(52) U.S. Cl.
  CPC ............. G06F 3/015 (2013.01); A61M 21/02 (2013.01); G06F 3/012 (2013.01); G06F 3/013 (2013.01); A61M 2021/0027 (2013.01); A61M 2021/005 (2013.01); A61M 2205/056 (2013.01); A61M 2205/3303 (2013.01); G06F 2203/011 (2013.01)

(58) Field of Classification Search
  CPC .......... G06F 3/015; G06F 3/012; G06F 3/013; G06F 2203/011; A61M 21/02; A61M 2021/0027; A61M 2021/005; A61M 2205/056; A61M 2205/3303
  See application file for complete search history.

(56) References Cited

U.S. PATENT DOCUMENTS

| | | | |
|---|---|---|---|
| 5,137,027 | A | 8/1992 | Rosenfeld |
| 7,429,108 | B2 | 9/2008 | Rosenberg |
| 8,979,545 | B2 | 3/2015 | Duffy |
| 9,596,508 | B2 | 3/2017 | McCoy et al. |

(Continued)

FOREIGN PATENT DOCUMENTS

| | | |
|---|---|---|
| CN | 105453070 A | 3/2016 |
| JP | 2018194931 A | 12/2018 |

(Continued)

OTHER PUBLICATIONS

Black, Rosemary, "Virtual Reality Programs Now Target Pain, Stress and Depression"; Published Jun. 24, 2020; pp. 1-6.

(Continued)

Primary Examiner — Jonathan A Boyd
(74) Attorney, Agent, or Firm — Thompson Hine LLP

(57) ABSTRACT

Devices, systems, and methods that provide content that distracts a user's attention away from discomfort, for example, occurring due to a prior injury or ongoing medical condition. The content is adjusted over time based on tracking the user's attentiveness towards the content. Specifically, the user's current attentive state may be tracked using physiological sensors and used to adapt content to mitigate the perception of discomfort. In some implementations, the user's stress is also assessed and used an indication of the user's current discomfort level to better track when the user's attentive state is shifting from the content to the discomfort and adjust the content accordingly.

31 Claims, 7 Drawing Sheets

(56) References Cited

U.S. PATENT DOCUMENTS

| | | | |
|---|---|---|---|
| 9,710,130 | B2 | 7/2017 | Mulcahy et al. |
| 10,231,614 | B2 | 3/2019 | Krueger |
| 10,303,245 | B2 | 5/2019 | Ha et al. |
| 10,620,700 | B2 | 4/2020 | Publicover et al. |
| 11,354,805 | B2 | 6/2022 | Yildiz |
| 11,861,837 | B2 | 1/2024 | Yildiz |
| 2006/0203197 | A1 | 9/2006 | Marshall |
| 2011/0262887 | A1 | 10/2011 | Cleveland |
| 2012/0083668 | A1 | 4/2012 | Pradeep et al. |
| 2014/0184550 | A1 | 7/2014 | Hennessey et al. |
| 2015/0130703 | A1 | 5/2015 | Ghajar |
| 2015/0213634 | A1 | 7/2015 | Kamarkar et al. |
| 2015/0297109 | A1 | 10/2015 | Garten et al. |
| 2015/0332166 | A1 | 11/2015 | Ferens et al. |
| 2016/0077547 | A1 | 3/2016 | Aimone et al. |
| 2016/0080874 | A1 | 3/2016 | Fullam |
| 2016/0196758 | A1 | 7/2016 | Causevic et al. |
| 2016/0225012 | A1 | 8/2016 | Ha et al. |
| 2016/0263345 | A1* | 9/2016 | Shuster .................. A61F 2/72 |
| 2016/0328015 | A1 | 11/2016 | Ha et al. |
| 2016/0372489 | A1 | 12/2016 | Li |
| 2017/0131766 | A1 | 5/2017 | He et al. |
| 2017/0293356 | A1 | 10/2017 | Khaderi et al. |
| 2017/0365101 | A1 | 12/2017 | Samec et al. |
| 2018/0139565 | A1 | 5/2018 | Norris |
| 2018/0184974 | A1 | 7/2018 | Cimenser et al. |
| 2018/0190309 | A1 | 7/2018 | Glasgow |
| 2018/0255167 | A1 | 9/2018 | Saito |
| 2018/0285442 | A1 | 10/2018 | Coleman et al. |
| 2018/0365491 | A1 | 12/2018 | Delaney |
| 2018/0365875 | A1 | 12/2018 | Yildiz |
| 2019/0019089 | A1 | 1/2019 | Baughman et al. |
| 2019/0033914 | A1 | 1/2019 | Aimone et al. |
| 2019/0108191 | A1 | 4/2019 | Frank |
| 2019/0163258 | A1 | 5/2019 | Baughman et al. |
| 2019/0175090 | A1 | 6/2019 | Reiner et al. |
| 2019/0200920 | A1* | 7/2019 | Tien .................. A61B 5/0205 |
| 2019/0239790 | A1 | 8/2019 | Gross et al. |
| 2019/0265802 | A1 | 8/2019 | Parshionikar |
| 2020/0089317 | A1 | 3/2020 | Ghajar |
| 2020/0089321 | A1 | 3/2020 | Kacelenga |
| 2020/0349337 | A1* | 11/2020 | Kameni .................. G06F 3/14 |
| 2021/0035298 | A1 | 2/2021 | Mldiz et al. |
| 2021/0298647 | A1 | 9/2021 | Axo et al. |
| 2022/0086592 | A1 | 3/2022 | McElveen et al. |
| 2022/0261999 | A1 | 8/2022 | Yildiz |
| 2023/0259203 | A1 | 8/2023 | Mulliken |
| 2023/0282080 | A1 | 9/2023 | Mulliken |
| 2024/0164677 | A1 | 5/2024 | Yildiz |

FOREIGN PATENT DOCUMENTS

| | | |
|---|---|---|
| WO | WO2013015730 A1 | 1/2013 |
| WO | WO2015072202 | 5/2015 |
| WO | WO2018100875 A1 | 6/2018 |
| WO | WO2019067731 A1 | 4/2019 |
| WO | WO2020159784 | 8/2020 |
| WO | WO2020227254 | 11/2020 |
| WO | WO2021150971 | 7/2021 |
| WO | 2021247310 A1 | 12/2021 |
| WO | 2021247312 A1 | 12/2021 |
| WO | 2022212070 A1 | 10/2022 |

OTHER PUBLICATIONS

Black, Rosemary, "Learn to Practice CBT and ACT at Home"; Published Oct. 21, 2019; pp. 1-4.

Bombeke, K. et al., "Do Not Disturb: Psychophysiological Correlates of Boredom, Flow and Frustration During VR Gaming," International Conference on Image Analysis and Processing (ICIAP), 17th International Conference, Naples, Italy, 19 pages. Sep. 2013 2013.

Kuziek, J. et al., "Real brains in virtual worlds: Validating a novel oddball paradigm in virtual reality," bioRxiv, 45 pages, https://www.biorxiv.org/content/10.1101/749192v3.full.pdf, Mar. 2020 2020.

Rizzo, A. et al., "Virtual Reality and Cognitive Assessment and Rehabilitation: The State of the Art," Virtual Reality in Neuro-Psycho-Physiology, Giuseppe Riva (Ed.), 26 pages. 1997 1997.

Bixler, Robert et al., "Automatic gaze-based user-independent detection of mind wandering during computerized reading," User Modeling and User-Adapted Interaction, Dordrecht, NL, vol. 26, No. 1, pp. 33-68, Sep. 2015 2015.

Parsons, T.D. and Reinebold, J.L., "Adaptive Virtual Environments for NeuropsychologicalGames," IEEE Transactions on Consumer Electronics, vol. 58, No. 2, May 2012 2012.

\* cited by examiner

ADAPTATION OF ELECTRONIC CONTENT

CROSS-REFERENCE TO RELATED APPLICATIONS

This application claims the benefit of U.S. Provisional Application Ser. No. 63/212,801 filed Jun. 21, 2021, which is incorporated herein in its entirety.

TECHNICAL FIELD

The present disclosure generally relates to presenting content via electronic devices, and in particular, to systems, methods, and devices that present content to mitigate the perception of discomfort or otherwise provide relief from discomfort, for example, discomfort due to a previous injury or ongoing medical condition.

BACKGROUND

A user's attentive state while experiencing discomfort can have a significant effect on how the user perceives the discomfort. Discomfort may feel less intense or otherwise be made more bearable, for example, by distracting a user's attention away from the discomfort.

SUMMARY

Various implementations disclosed herein include devices, systems, and methods that provide content (e.g., an extended reality (XR) environment) that distracts a user's attention away from discomfort, e.g., pain. The content is adjusted over time based on tracking the user's attentiveness towards the content. Specifically, the user's current attentive state may be tracked using physiological sensors and used to adapt visual/audio content so that the user experiences a better reduction in his or her perception of discomfort than would be experienced given non-adaptive content. For example, some implementations may identify that the user's eye characteristics (e.g., blink rate, stable gaze direction, saccade amplitude/velocity, and/or pupil radius) and/or facial expression correspond to a "focused on content" attentive state rather than a "focused on discomfort" attentive state. In some implementations, the user's stress is also assessed and used an indication of the user's current discomfort level to better track when the user's attentive state is shifting from the distracting content to the discomfort and the content is adjusted accordingly. Based on tracking the user's attentive state (and its changes) over time, content presented to the user may be adapted to provide a desirable reduction or mitigation of the user's perception of discomfort.

In some implementations, a device (e.g., a handheld, laptop, desktop, or head-mounted device (HMD)) provides content (e.g., an XR environment) to a user. The device obtains, with one or more sensors, physiological data (e.g., pupil data, eye gaze data, electroencephalography (EEG) data, heartrate, facial expression data, etc.) associated with the user. Based on the obtained physiological data, the techniques described herein can determine a user's attentive state (e.g., attentive to content, attentive to discomfort, etc.). Based on the physiological data and associated attentive state, the techniques can adjust content and/or provide feedback to the user or persons assisting the user such as his or her doctor's or therapists.

Some implementations provide a non-transitory computer-readable storage medium storing program instructions executable by one or more processors to perform operations of a method. The operations of the exemplary method include presenting content to a user in an extended reality (XR) environment (e.g., presenting stimuli to distract the user from discomfort) and obtaining physiological data associated with the user via one or more physiological sensors.

The operations of the exemplary method include determining an attentive state of the user based on the physiological data, where the user may be perceiving discomfort and the attentive state of the user is associated with whether (or how much) attention of the user is directed to the content versus the discomfort. In some implementations, this involves measuring gaze (e.g., gaze stability and/or direction) to measure how well the user is paying attention to/how engaged the user is engaged with distracting content versus his or her discomfort. In some implementations, the attentive state of the user being directed to discomfort or not is determined based on tracking facial gestures and/or facial expressions. In some implementations, the attentive state is determined based on assessing whether the user is mind wandering, which may be indicative that the user's attention has focused on his or her discomfort rather than on presented content.

In some implementations, the attentive state may also be based on using stress (e.g., detected via physiological sensor(s)) as a proxy for attention to discomfort. Stress may be measured and tracked over time to identify instances or time periods during which a user's attention has switched to focus more on discomfort than during prior periods. For example, detection of a spike in stress level over a short period of time may be indicative of a user's attention shifting to focus on an uncomfortable sensation.

The operations of the exemplary method further include determining a modification to the content based on the attentive state of the user and presenting the modified content. For example, this may include dynamically changing the content, moving the content in a way configured to draw the user's attention to the content, enlarging content to draw attention to the content, changing contrast of content to make the content more easily perceptible, increasing volume or changing spatialization of audible content to draw attention to the content, and/or extending the period of time during which the content is presented, as examples. The modification of the content may shift the user's attention away from his or her discomfort and thus, over a period of time, help ensure that a user is distracted from (and therefore less burdened by) his or her discomfort.

Distraction from discomfort using the techniques disclosed herein may provide numerous benefits to users. Such distraction may reduce the perception of discomfort and reduce a user's need for and/or reliance upon discomfort relief medication, and ultimately lower risks associated with developing dependence upon opioids and other such discomfort medications. Discomfort is a general term that describes uncomfortable sensations in the body and stems from activation of the nervous system. Discomfort can range from annoying to debilitating and may be experienced by or perceived by different people in different way. Discomfort may be experienced as a sharp stab, a dull ache, throbbing, pinching, stinging, burning, or soreness. Recognizing that discomfort may be a subjective feeling experienced or otherwise perceived by users in different ways, implementations disclosed herein may generally improve a user experiences when a user is perceiving an uncomfortable sensation by mitigating the perception of the discomfort. For example, a user may perceive the sharpness of an uncomfortable sensation at a particular level and may experience the same uncomfortable sensation as at a lesser level based on distraction provided by one or more of the techniques disclosed herein. Such mitigation may substantially improve a user's experience. The mitigation of the perception of discomfort may also enable patients to be ambulatory sooner after a surgical procedure. The mitigation of the perception of discomfort may help patients resolve fears of certain medical techniques and procedures, e.g., needle-phobia. The techniques disclosed herein may be used to help users with discomfort, including but not limited to aches, undesirable sensations, acute pain, and chronic pain.

In accordance with some implementations, a non-transitory computer readable storage medium has stored therein instructions that are computer-executable to perform or cause performance of any of the methods described herein. In accordance with some implementations, a device includes one or more processors, a non-transitory memory, and one or more programs; the one or more programs are stored in the non-transitory memory and configured to be executed by the one or more processors and the one or more programs include instructions for performing or causing performance of any of the methods described herein.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

Figure 2:
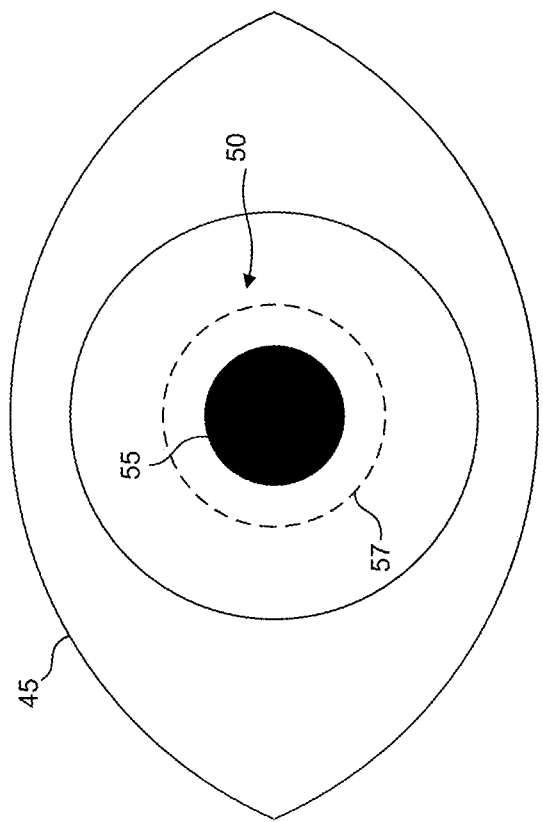
FIG. 2 illustrates a pupil of the user of FIG. 1 in which the diameter of the pupil varies with time in accordance with some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects or variants do not include all of the specific details described herein. Moreover, well-known systems, methods, components, devices and circuits have not been described in exhaustive detail so as not to obscure more pertinent aspects of the example implementations described herein.

Figure 1:
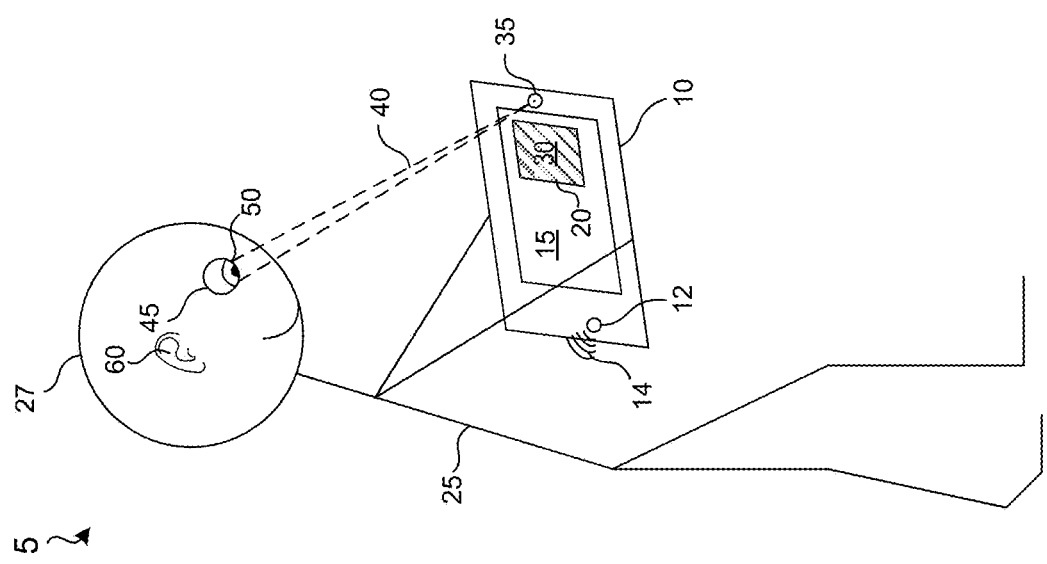
FIG. 1 illustrates a device displaying content and obtaining physiological data from a user in accordance with some implementations.

FIG. 1 illustrates a real-world environment 5 including a device 10 with a display 15. In some implementations, the device 10 displays content 20 to a user 25, and a visual characteristic 30 that is associated with content 20. For example, content 20 may be text, an image, a graphic, a video, interactive content, instructions, guidance, etc. In some implementations, the visual characteristic 30 associated with content 20 includes visual characteristics such as size, shape, contrast, hue(s), saturation level(s), spatial frequencies, motion, highlighting, etc. For example, content 20 may be displayed with a visual characteristic 30 of green highlighting covering or surrounding content 20. The content 20 itself and/or the visual characteristic 30 may be modified to improve the effectiveness of the content 20 with respect to distracting the user 25 from discomfort. In some implementations, the visual experience (e.g., content 20) can occupy the entire display area of display 15. For example, during a distracting experience, content 20 may be an entertaining video or sequence of images. In some implementations, content 20 may be a visual experience (e.g., a distracting experience), for example, including a view of a three-dimensional (3D) environment or an extended reality (XR) environment.

As used herein, the phrase "experience" refers to a period of time during which a user uses one or more electronic devices and has one or more attentive states. In one example, a user has an experience while holding, wearing, or being proximate to an electronic device that includes one or more sensors that obtain physiological data to assess one or more characteristics that are indicative of the user's attentional state. In another example, a user has an experience in which the user perceives content displayed by an electronic device while the same or another electronic obtains physiological data (e.g., pupil data, EEG data, etc.) to assess the user's attentive state. In another example, a user has an experience in which the user holds, wears, or is proximate to an electronic device that provides a series of audible or visual instructions that guide the experience. For example, the instructions may instruct the user to focus on his or her attention on his or her breath, etc. During such an experience, the same or another electronic device may obtain physiological data to assess the user's attentive state. In the example of FIG. 1, the device 10 obtains physiological data (e.g., pupil size data, eye gaze data, etc.) from the user 25 via a sensor 35. While this example and other examples discussed herein illustrate a single device 10 in a real-world environment 5, the techniques disclosed herein are applicable to multiple devices and multiple sensors, as well as to other real-world environments/experiences. For example, the functions of device 10 may be performed by multiple devices.

In some implementations, the device 10 includes an eye tracking system for detecting eye position and eye movements. For example, an eye tracking system may include one or more infrared (IR) light-emitting diodes (LEDs), an eye tracking camera (e.g., near-IR (NIR) camera), and an illumination source (e.g., an NIR light source) that emits light (e.g., NIR light) towards the eyes of the user 25. Moreover, the illumination source of the device 10 may emit NIR light to illuminate the eyes of the user 25 and the NIR camera may capture images of the eyes of the user 25. In some implementations, images captured by the eye tracking system may be analyzed to detect position and movements of the eyes of the user 25, or to detect other information about the eyes such as pupil dilation or pupil diameter. Moreover, the point of gaze estimated from the eye tracking images may enable gaze-based interaction with content shown on the near-eye display of the device 10.

In some implementations, the device 10 employs various physiological sensor, detection, or measurement systems. Detected physiological data may include, but is not limited to, EEG, electrocardiography (ECG), electromyography (EMG), functional near infrared spectroscopy signal (fNIRS), blood pressure, skin conductance, or pupillary response. In some implementations, sensors capture data (e.g., images, depth data, temperature data, vibration data, etc.) about the skin and/or shape of a person's face from which facial gestures (micro or macro gestures) and/or facial expressions may be identified. Moreover, the device 10 may simultaneously detect multiple forms of physiological data in order to benefit from synchronous acquisition of physiological data. Moreover, in some implementations, the physiological data represents involuntary data, e.g., responses that are not under conscious control. For example, a pupillary response may represent an involuntary movement.

In some implementations, one or both eyes 45 of the user 25, including one or both pupils 50 of the user 25 present physiological data in the form of a pupillary response (e.g., pupillary data 40). The pupillary response of the user 25 results in a varying of the size or diameter of the pupil 50, via the optic and oculomotor cranial nerve. For example, the pupillary response may include a constriction response (miosis), e.g., a narrowing of the pupil, or a dilation response (mydriasis), e.g., a widening of the pupil. In some implementations, the device 10 may detect patterns of physiological data representing a time-varying pupil diameter.

In some implementations, a pupillary response may be in response to auditory content that one or both ears 60 of the user 25 detect. For example, device 10 may include a speaker 12 that projects sound via sound waves 14. The device 10 may include other audio sources such as a headphone jack for headphones, a wireless connection to an external speaker, and the like.

FIG. 2 illustrates a pupil of the user 25 of FIG. 1 in which the diameter of the pupil varies with time. Pupil diameter tracking may be potentially indicative of an attentive state of a user. As shown in FIG. 2, a present attentive state (e.g., present pupil diameter 55) may vary in contrast to a past attentive state (e.g., past pupil diameter 57). For example, the present state may include a present pupil diameter and a past state may include a past pupil diameter. The physiological data may vary in time and the device 10 may use the physiological data to measure one or both of a user's physiological characteristics, including attentive state, stress, etc. In some implementations, the physiological data may include the physiological response to a visual or an auditory stimulus of a radius of the pupil after the user 25 glances at content 20, measured via eye-tracking technology (e.g., via an HMD).

Returning to FIG. 1, in some implementations, as illustrated in FIG. 1, the device 10 is a handheld electronic device (e.g., a smartphone or a tablet). In some implementations the device 10 is a laptop computer or a desktop computer. In some implementations, the device 10 has a touchpad and, in some implementations, the device 10 has a touch-sensitive display (also known as a "touch screen" or "touch screen display"). In some implementations, the device 10 is a wearable head mounted display (HMD).

In some implementations, the device 10 has a graphical user interface (GUI), one or more processors, memory and one or more modules, programs or sets of instructions stored in the memory for performing multiple functions. In some implementations, the user 25 interacts with the GUI through finger contacts and gestures on the touch-sensitive surface, an input device, audible commands, and/or gaze interactions. In some implementations, the functions include image editing, drawing, presenting, word processing, website creating, disk authoring, spreadsheet making, game playing, telephoning, video conferencing, e-mailing, instant messaging, workout support, digital photographing, digital videoing, web browsing, digital music playing, and/or digital video playing. Executable instructions for performing these functions may be included in a computer readable storage medium or other computer program product configured for execution by one or more processors.

As used herein, the phrase "physical environment" refers to a physical world that people can sense and/or interact with without aid of electronic devices. The physical environment may include physical features such as a physical surface or a physical object. For example, the physical environment corresponds to a physical park that includes physical trees, physical buildings, and physical people. People can directly sense and/or interact with the physical environment such as through sight, touch, hearing, taste, and smell. In contrast, an extended reality (XR) environment refers to a wholly or partially simulated environment that people sense and/or interact with via an electronic device. For example, the XR environment may include augmented reality (AR) content, mixed reality (MR) content, virtual reality (VR) content, and/or the like. With an XR system, a subset of a person's physical motions, or representations thereof, are tracked, and, in response, one or more characteristics of one or more virtual objects simulated in the XR environment are adjusted in a manner that comports with at least one law of physics. As one example, the XR system may detect head movement and, in response, adjust graphical content and an acoustic field presented to the person in a manner similar to how such views and sounds would change in a physical environment. As another example, the XR system may detect movement of the electronic device presenting the XR environment (e.g., a mobile phone, a tablet, a laptop, or the like) and, in response, adjust graphical content and an acoustic field presented to the person in a manner similar to how such views and sounds would change in a physical environment. In some situations (e.g., for accessibility reasons), the XR system may adjust characteristic(s) of graphical content in the XR environment in response to representations of physical motions (e.g., vocal commands).

There are many different types of electronic systems that enable a person to sense and/or interact with various XR environments. Examples include head mountable systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld controllers with or without haptic feedback), smartphones, tablets, and desktop/laptop computers. A head mountable system may have one or more speaker(s) and an integrated opaque display. Alternatively, a head mountable system may be configured to accept an external opaque display (e.g., a smartphone). The head mountable system may incorporate one or more imaging sensors to capture images or video of the physical environment, and/or one or more microphones to capture audio of the physical environment. Rather than an opaque display, a head mountable system may have a transparent or translucent display. The transparent or translucent display may have a medium through which light representative of images is directed to a person's eyes. The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In some implementations, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

Figure 3:
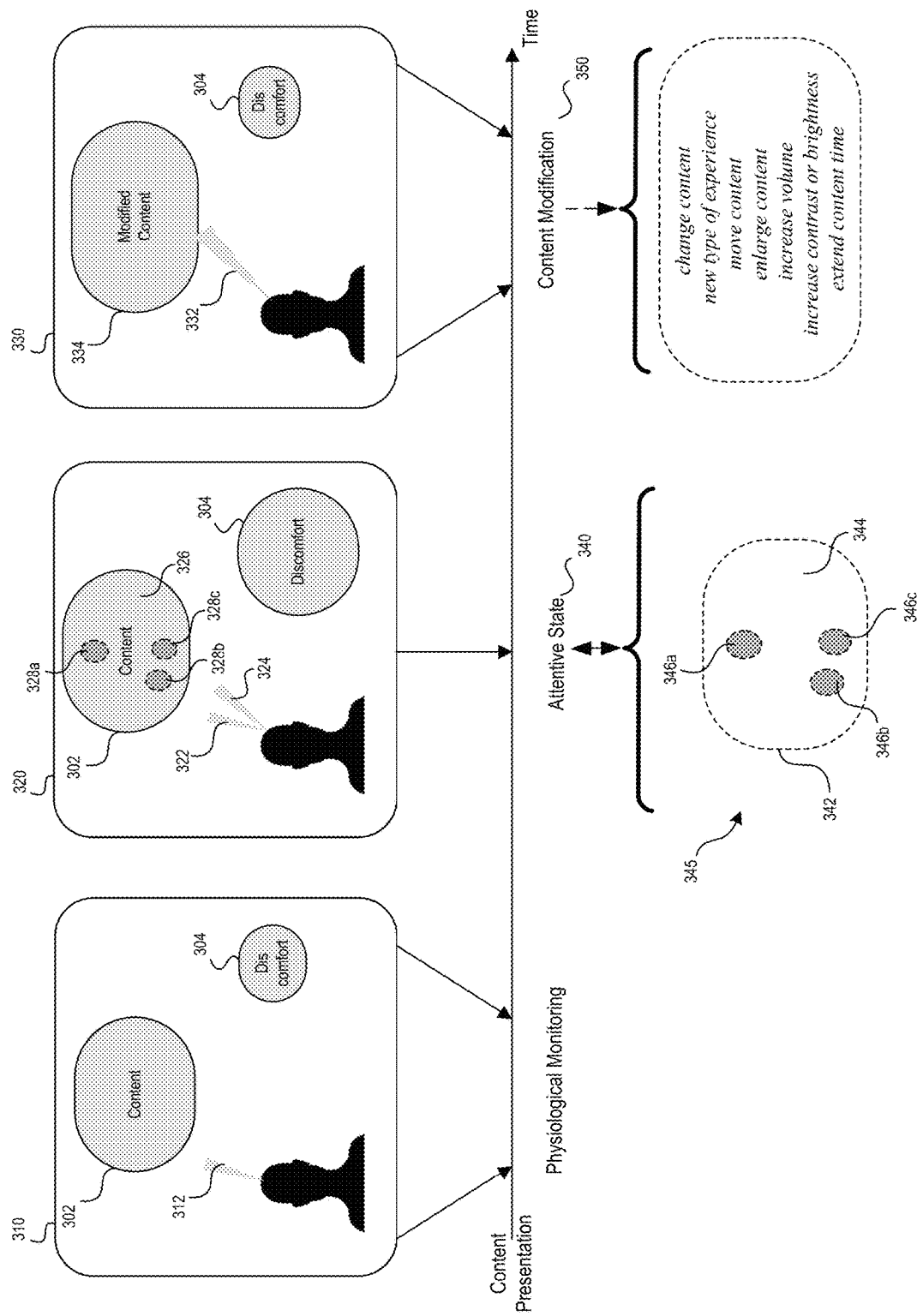
FIG. 3 illustrates assessing an attentive state of the user viewing content based on physiological data in accordance with some implementations.

FIG. 3 illustrates assessing an attentive state 340 of the user viewing content based on physiological data. In particular, FIG. 3 illustrates a user (e.g., user 25 of FIG. 1) being presented with content 302 during while the user may be perceiving discomfort 304 and where the user, via obtained physiological data, has a physiological response (e.g., the user looks towards portions of the content as detected by eye gaze characteristic data). For example, at content presentation instant 310, a user (e.g., user 25) is being presented with content 302 that includes visual content (e.g., a cooking video), and the user's pupillary data 312 is monitored as a baseline. Then, at content presentation instant 320, the user's physiological data (e.g., pupillary data 322 and 324 corresponding to transitional eye movement within the content 302) is being monitored for any physiological response.

Identification of eye movement between relevant and non-relevant areas of the content 302 by a content analysis instruction set, e.g., using an attention map instruction set, may indicate an attentive state 340 in which the user is attentive to discomfort more than the content 302. For example, content 302 may include one or more people, important (e.g., relevant) objects, or other objects that are within view of the user. For example, content area 328a may be an area of content within content 302 that is of a face of a person talking to the camera (e.g., a cook in a cooking instructional video). Content areas 328b and 328c may be an area of relevant content within content 302 that includes an object or several objects that are important to the video (e.g., food that is being prepped, cooking utensils, etc.). Alternatively, content area 328b and/or 328c may be an area of relevant content within content 302 that includes the hands of the person talking to the camera (e.g., hands of the cooking instructor holding the food or cooking utensils). Identification that a user's gaze is variable, not focused on relevant portions of content 302, or focused on irrelevant portions of content 302 may be indicative of an attentive state 340 in which the user is attentive to something other than the content 302, e.g., more attentive to discomfort.

The user's attention to content may be assessed using an attention map. An attention map 345 may be obtained prior to or generated during the content presentation. The attention map 345 can be utilized to track the overall context of what the user is focused on during the presentation of content 302. For example, the attention map 345 includes content area 342 associated with the viewing area of content 302. The attention map includes relevant areas 346a, 346b, 346c that are associated with the content areas 328a, 328b, and 328c, respectively. Additionally, attention map 345 designates the remaining area (e.g., any area within content area 342 determined as not relevant) as non-relevant area 344. The attention map can be utilized to determine when a user scans content 302 between relevant and non-relevant areas to determine to what the user paying attention. For example, a user may constantly be transitioning between relevant areas 346a, 346b, and 346c, but then would need to scan over non-relevant area 344 during those transitions. This scanning or transitioning may also include a brief amount of time the user glances at another portion of the content 302 to look at the background or a non-relevant person or object in the background before scanning back to a relevant object 346. This "transition" (e.g., transition between an eye gaze towards a relevant area versus a non-relevant area) may be considered by an attention map algorithm as being indicative of an attentive state towards the content if the transitions are made in less than a threshold amount of time (e.g., transitioning between a relevant and non-relevant area in less than 1 second). Additionally, or alternatively, an average number of transitions between relevant and non-relevant areas may tracked over time (e.g., a number of transitions per minute) to determine an attentive state. For example, more frequent and quicker transitions may be used to determine that a user is being attentive (e.g., the user is engaged with the content presentation) versus slower transitions (e.g., the user is focusing on discomfort).

In some implementations, presentation of content 302 is processed by an attention map instruction set for a first time (e.g., new content, such as a new video for cooking instructions). For example, a cooking instructional video that has not been seen before by the user nor been analyzed before may be analyzed by an attention map instruction set. The relevant and non-relevant areas of content 302 (e.g., relevant areas 346a—c and non-relevant area 344) may be determined in real time. Relevance may be determined based on analyzing the content 302 and/or based on the physiological data acquired during the content presentation (e.g., the user's pupillary data 322 and 324). For example, the content areas 328a-c may be determined to be relevant areas versus non-relevant areas based on various image processing and machine learning techniques (e.g., object detection, facial recognition, and the like).

Alternatively, in some implementations, the content areas 328a—c may be identified as "relevant objects" via an attention map 345. For example, an attention map instruction set may have already analyzed content 302 (e.g., the cooking instructional video) and the relevant and non-relevant areas of content 302 (e.g., relevant areas 346a— c and non-relevant area 344) may already be known by the system. Thus, the analysis of the attentive state of the user may be more accurate with already known content than content that is being shown and analyzed for the first time as the user is viewing it.

After a segment of time after the physiological data (e.g., the user's pupillary data 322 and 324) is analyzed (e.g., by an attention map instruction set), content presentation instant 330 is presented to the user with modified content 334 determined based on the attentive state 340 assessment, e.g., based on whether the user was attentive to content or discomfort. The content modification 350 may produce the modified content 334 by changing the content 302, introducing movement within the content 302, changing the type of experience provided by the content 302, moving content 302, enlarging content 302, increasing volume, and/or increasing contrast or brightness, as examples. The modified content 334 may be generated by changing the content 302 to draw the user's attention to the content, to make the content more easily perceptible, and/or change level of immersion provided by the experience to renew the user's focus on the experience.

Additionally, or alternatively, the modified content 334 may be an offline or real-time statistical analysis and attention summary that is provided to the user. In one example, the system tracks attentional states throughout several days and weeks and provides content configured to retain the user's attention during those days and times. In one example, an attention graph is provided to a user (e.g., real-time during a session, or following the session as a summary) that plots duration of the session on the x-axis and average attentional state of the user on the y-axis. For example, an attention graph can summarize how a user's attention to content versus discomfort decreases as session duration increases. This analysis could provide a certain level of awareness to the user about the user's attentiveness to discomfort during one or more periods of time. In some implementations, the system could also provide a summary to the user of his or her "most helpful" content, i.e., the content or types of content that had the most success with respect to mitigating the user's attention to discomfort.

As illustrated in FIG. 3, the user's pupillary data 332 demonstrates that the user eye gaze was drawn towards the modified content 334. The user physiological content to the modified content 334 may be monitored and used to make further adjustments and adaptions to content. Accordingly, the user's attentive state 340 assessment can be continuously monitored throughout the presentation of content and used to adapt the content in real-time to provide the user with an optimal experience.

The modified content 334 may include a visual presentation. For example, an icon may appear, or a text box may appear instructing the user to pay attention. In some implementations, the modified content 334 may include an auditory stimulus. For example, spatialized audio may be presented at one or more of the relevant content areas 328 to redirect the user's attention towards the relevant areas of the content presentation (e.g., if determined the user not attentive to the content 302). In some implementations, the modified content 334 may include an entire display of visual content (e.g., flashing yellow over the entire display of the device.) Alternatively, the modified content 334 may include visual content framing other content (e.g., on a mobile device, a virtual frame of the display be created to acquire the user's attention). In some implementations, the modified content 334 may include a combination of visual content and an auditory stimulus. For example, a notification window or arrow may direct the user to the relevant content areas 328 and an audio signal may be presented that directs the user to "watch closely" as the cooking instructor is preparing the food in the instructional video. These visual and/or auditory cues can help direct the user to pay more attention to the relevant areas of a video.

Figure 4:
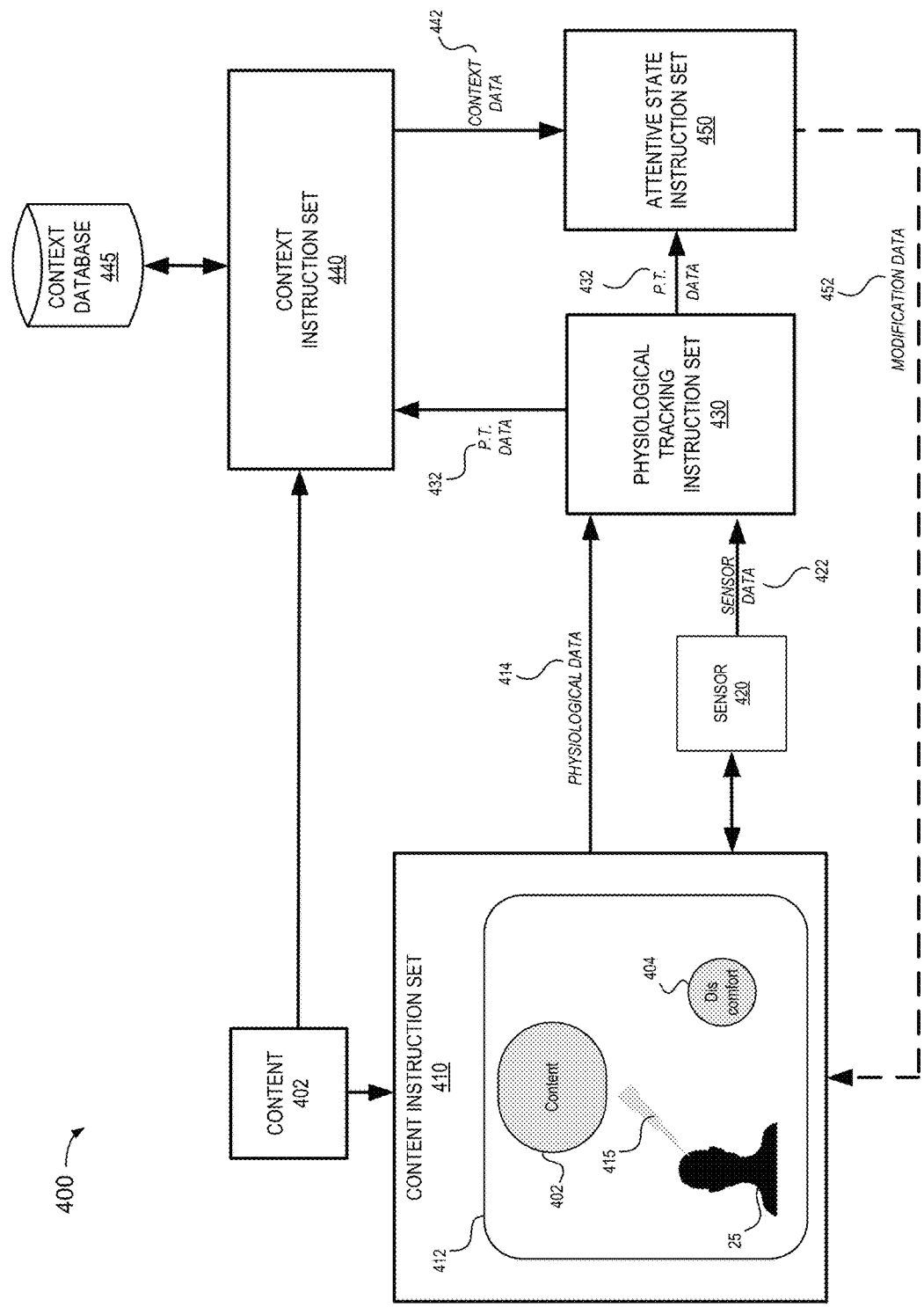
FIG. 4 illustrates a system diagram for assessing an attentive state of the user viewing content based on physiological data in accordance with some implementations.

FIG. 4 is a system flow diagram of an example environment 400 in which an attentive state assessment system can assess an attentive state of a user viewing content based on physiological data and provide a provide modified content. In some implementations, the system flow of the example environment 400 is performed on a device (e.g., device 10 of FIG. 1), such as a mobile device, desktop, laptop, or server device. The content of the example environment 400 can be displayed on a device (e.g., device 10 of FIG. 1) that has a screen (e.g., display 15) for displaying images and/or a screen for viewing stereoscopic images such as an HMD. In some implementations, the system flow of the example environment 400 is performed on processing logic, including hardware, firmware, software, or a combination thereof. In some implementations, the system flow of the example environment 400 is performed on a processor executing code stored in a non-transitory computer-readable medium (e.g., a memory).

The system flow of the example environment 400 acquires and presents content to a user, analyzes the content for context, obtains physiological data associated with the user during presentation of the content, assesses an attentive state of the user based on the physiological data of the user, and modifies the content based on the attentive state (e.g., based on a change from attentive/focused on content to attentive to discomfort). For example, an attentive state assessment technique described herein determines, based on obtained physiological data, a user's attentive state (e.g., attentive to content, attentive to discomfort, etc.) and provides modified content based on the attentive state of the user, e.g., to recharge or spur renewed attention in the content and improve the effectiveness of the content in distracting the user from the perception of the discomfort.

The example environment 400 includes a content instruction set 410 that is configured with instructions executable by a processor to provide and/or track content 402 for display on a device (e.g., device 10 of FIG. 1). For example, the content instruction set 410 provides content presentation instant 412 that includes content 402 to a user 25. For example, content 402 may include image(s) and sound data (e.g., a video). The content presentation instant 412 could be an XR environment (e.g., a view of 3D environment with real and/or virtual content). The user could be wearing an HMD and looking at a real physical environment either via a live camera view through the device, such as wearing smart glasses that user can see through, while also be presented with virtual visual and/or audio content. During an experience, while a user 25 is viewing the content 402, physiological data, such as pupillary data 415 (e.g., pupillary data 40 such as eye gaze characteristic data) of the user's eyes, can be monitored and sent as physiological data 414.

The environment 400 includes a physiological tracking instruction set 430 to track a user's physiological attributes as physiological tracking data 432 using one or more of the techniques discussed herein or as otherwise may be appropriate. For example, the physiological tracking instruction set 430 may acquire physiological data 414 (e.g., pupillary data 415) from the user 25 viewing the content 402. Additionally, or alternatively, a user 25 may be wearing a sensor 420 (e.g., an EEG sensor, a vibration sensor, a motion sensor, etc.) that generates sensor data 422 (e.g., EEG data) as additional physiological data. Thus, as the content 402 is presented to the user as content presentation instant 412, the physiological data 414 (e.g., pupillary data 415) and/or sensor data 422 is sent to the physiological tracking instruction set 430 to track a user's physiological attributes as physiological tracking data 432, using one or more of the techniques discussed herein or as otherwise may be appropriate.

In an example implementation, the environment 400 further includes a context instruction set 440 that is configured with instructions executable by a processor to obtain content and physiologic tracking data and generate context data (e.g., identifying relevant and non-relevant areas of the content 402 via an attention map). For example, the context instruction set 440 acquires content 402 and physiologic tracking data 432 from the physiological tracking instruction set 430 and determines context data 442 based on identifying relevant areas of the content while the user is viewing the presentation of the content 402 (e.g., a first time viewed content). Alternatively, the context instruction set 440 selects context data associated with content 402 from a context database 445 (e.g., if the content 402 was previously analyzed by the context instruction set, i.e., a previously viewed/analyzed context). In some implementations, the context instruction set 440 generates an attention map associated with content 402 as the context data 442. For example, the attention map (e.g., attention map 345 of FIG. 3) can be utilized to track the overall context of what the user is focused on during the presentation of content 402. For example, as discussed herein for FIG. 3, an attention map includes a content area associated with the viewing area of content, relevant areas that are associated with identified content areas of the content (e.g., facial recognition, object detection, etc.), and non-relevant areas.

In an example implementation, the environment 400 further includes an attentive state instruction set 450 that is configured with instructions executable by a processor to assess the attentive state (e.g., attentive state such as focused on content or focused on discomfort, etc.) of a user based on a physiological data (e.g., eye gaze, pupil dilation, facial gestures, facial expressions, etc.) using one or more of the techniques discussed herein or as otherwise may be appropriate. For example, the attentive state instruction set 450 acquires physiological tracking data 432 from the physiological tracking instruction set 430 and context data 442 from the context instruction set 440 (e.g., attention map data) and determines the attentive state of the user 25 during the presentation of the content 402. An attention map may provide a scene analysis that can be used by the attentive state instruction set 450 to understand what the person is looking at and improve the determination of the attentive state. In some implementations, the attentive state instruction set 450 can then provide modification data 452 (e.g., visual and/or audible content changes) to the content instruction set 410 based on the attentive state assessment.

Some implementations adjust content provided in an XR environment to distract a user from discomfort based on tracking the user's attentiveness towards the distracting content. The user's current attentive state may be tracked using physiological sensors and used to adjust visual/audio content in a closed loop manner. Stress detection may additionally be used as a proxy for discomfort to better to determine when a user's attentive state is returning specifically to the discomfort.

Figure 5:
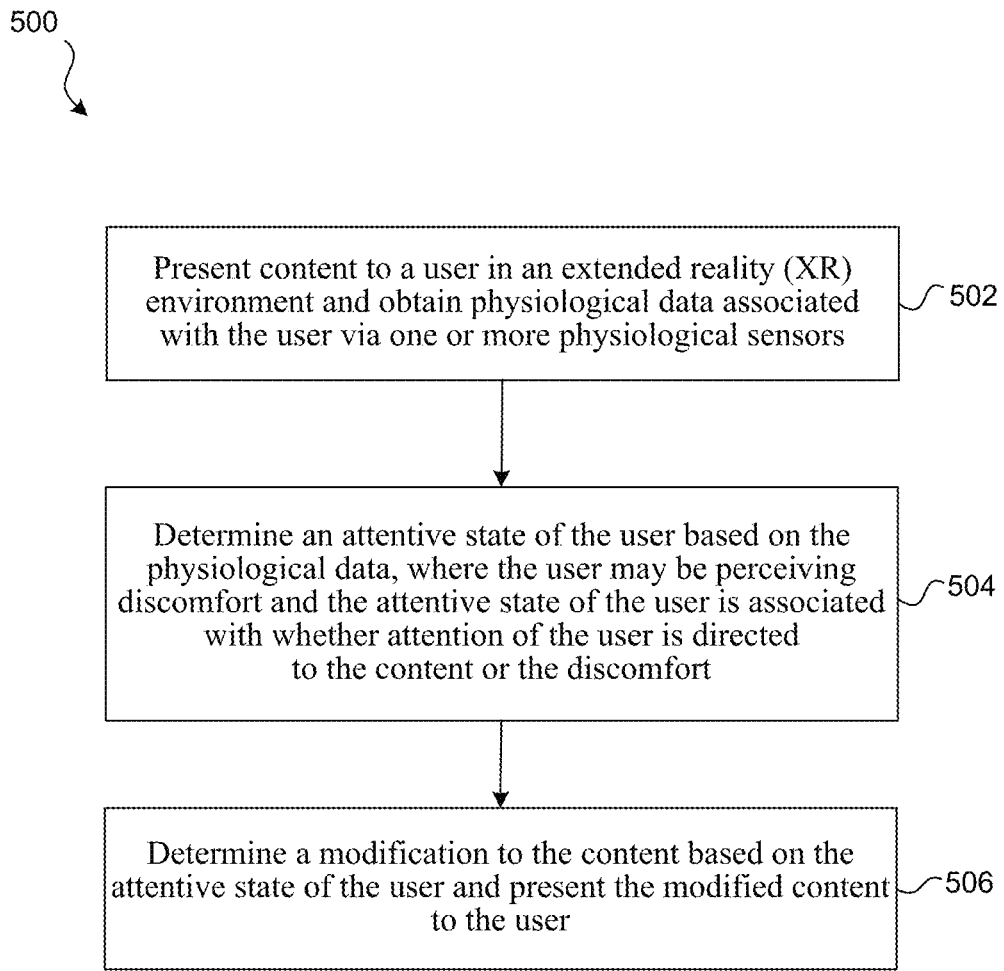
FIG. 5 is a flowchart representation of a method for presenting content to a user to mitigate perception of discomfort in accordance with some implementations.

FIG. 5 is a flowchart illustrating an exemplary method 500. In some implementations, a device such as device 10 (FIG. 1) performs the techniques of method 500 to present content to a user to mitigate perception of discomfort. In some implementations, the techniques of method 500 are performed on a mobile device, desktop, laptop, HMD, or server device. In some implementations, the method 500 is performed on processing logic, including hardware, firmware, software, or a combination thereof. In some implementations, the method 500 is performed on a processor executing code stored in a non-transitory computer-readable medium (e.g., a memory).

At block 502, the method 500 presents content to a user in an extended reality (XR) environment (e.g., presenting stimuli to distract the user from discomfort) and obtains physiological data associated with the user via one or more physiological sensors. The physiological data may be obtained via one or more sensors on a device worn by the user (e.g., on an HMD, watch, etc.), a device held by the user, and/or a device located within the same physical environment as the user. In some implementations, the physiological data includes pupil size, pupil dilation, pupil modulation, eye gaze saccades, electroencephalogram (EEG) amplitude, EEG frequency, facial shape, facial characteristics, facial expressions, facial gestures, and the like. In one example, obtaining the physiological data may involve obtaining images of the eye from which gaze direction/movement can be determined. In another example, obtaining physiological data comprises obtaining or electrooculography signal (EOG) data from which gaze direction/movement can be determined.

In some implementations, obtaining the physiological data includes monitoring for a response or lack of response occurring within a predetermined time following the presenting of the content, e.g., a particular event, trigger, or attentiveness test provided within the content. For example, the system may wait for up to five seconds after an event within the content to determine if a user looks in a particular direction (e.g., a physiological response).

Some implementations obtain physiological data and other user information to improve a user experience. In such processes, user preferences and privacy should be respected, as examples, by ensuring the user understands and consents to the use of user data, understands what types of user data are used, has control over the collection and use of user data and limiting distribution of user data, for example, by ensuring that user data is processed locally on the user's device. Users should have the option to opt in or out with respect to whether their user data is obtained or used or to otherwise turn on and off any features that obtain or use user information. Moreover, each user will have the ability to access and otherwise find out anything that the system has collected or determined about him or her. User data is stored securely on the user's device. User data that is used as input to a machine learning model should be stored securely on the user's device, for example, to ensure the user's privacy. The user's device may have a secure storage area, e.g., a secure enclave, for securing certain user information, e.g., data from image and other sensors that is used for eye-based identification, face identification, or other biometric identification. The user data associated with the user's body and/or attentive state may be stored in such a secure enclave and access/transmission of the user data to other devices restricted to ensure that the user data is kept securely on the user's device. User data may be prohibited from leaving the user's device and may be used only in machine learning models and other processes on the user's device.

At block 504, the method 500 determines an attentive state of the user based on the physiological data, where the user may be perceiving discomfort and the attentive state of the user is associated with whether attention of the user is directed to the content or the discomfort. This may involve evaluating the user's gaze (e.g., stability and/or direction) to measure how well the user is paying attention to/how engaged the user is with content versus being attentive to discomfort. Whether the user is mind wandering may be assessed based on an assumption that mind wandering may be indicative that the user's attention has shifted to focus on his or her discomfort.

In some implementations, techniques are used to distinguish between circumstances in which the user's mind is wandering due to discomfort from circumstances in which the user's mind wandering is triggered by something else. For example, this may involve detecting that a user's attention is shifting away from the content and observing a discomfort response (or lack thereof) based on stress detection. Detecting both an attention shift and a discomfort response occurring within a window of time, e.g., a threshold time period, may be provide a reliable indication that mind wandering is due to discomfort rather than something else, e.g., enabling a determination that this mind wandering is most likely directed towards discomfort and not some other kind of trigger (e.g., boredom). In some implementations, a source of detected mind wandering is identified based on additional or alternative information. For example, given an identified discomfort location on the user, e.g., a known spatially localized discomfort source in the user's arm, and a user's current actions indicating interest in that location may be used to determine that mind wandering is being triggered by discomfort in the arm. For example, sensors on the device may be used to detect that the user is rubbing, massaging, squeezing, or otherwise touching an injured body part, moving the injured body part, and/or gazing at the injured body part. Such information may be used to determine that the user's mind wandering is being triggered by the discomfort rather than by something else, e.g., boredom. In some implementations, the system may detect mind wandering, detect a stress response (possibly caused by discomfort), and detect a user action indicating interest in an injured portion of his or her body known to be associated with the discomfort, and these detections may together (e.g., occurring within a time period) provide information used to conclude that the user's mind wandering has been triggered by discomfort rather than by something else.

One or more gaze characteristics may be determined, aggregated, and used to classify the user's attentive state using statistical or machine learning techniques. In some implementations, the physiological data may be compared with the user's own prior data or typical user data to similar content of a similar experience.

In some implementations, attentive state is determined based on using the physiological data to measure gaze or body stability, a level of attentiveness to the content, and/or based on tracking gaze direction to track when the user is gazing at the content.

In some implementations, the user's attentive state is further determined based on assessing attention to discomfort based on tracking stress of the user based on the physiological data. Stress may be tracked based on heart rate, respiration rate, eye characteristics, body temperature, and/or EEG pattern identified based on the physiological data. Examples of using stress detection and/or measurement as a proxy for discomfort in determining or assessing a user's attention to discomfort are described with reference to FIG. 6 herein.

Facial gestures and/or facial expressions may be used to infer a discomfort percept and/or emotional state. In some implementations, the user's attentive state is at least partially inferred based on a facial gesture, which may be determined via physiological sensor data and/or images of the user's face, etc. For example, wincing may be interpreted as an indication of a sudden, new, or relatively high level of discomfort. Micro-gestures, which may be difficult or impossible to detect by human observation, may be assessed to assess the user's stress level and/or attention to discomfort. Similarly, vocalizations, e.g., grunts, moans, sighs, etc., by the user may be captured and used to identify stress, discomfort, and/or attentive state. In another example, a user's movement is used as an indication of stress, discomfort, and/or attentive state. For example, a sudden restriction of movement or slowing of movement may indicate the onset of discomfort, a change in the intensity of discomfort, or increased attention to discomfort.

In some implementations, determining that the user has a first attentive state includes determining a level of attentiveness towards presented content. For example, levels of attentiveness can be based on a number of transitions from relevant and non-relevant areas of the content presented (e.g., relevant areas 346 compared to non-relevant area 344 of FIG. 3). The system could determine a level of attentiveness as an attention barometer that can be customized based on the type of content shown during the user experience.

In some implementations, attentive state may be determined using statistical or machine learning-based classification techniques. For example, determining that the user has a first attentive state includes using a machine learning model trained using ground truth data that includes self-assessments in which users labelled portions of experiences with labels (e.g., focused, distracted by discomfort, etc.). For example, to determine the ground truth data that includes self-assessments, a group of subjects, while watching entertaining content, could be prompted at different time intervals (e.g., every 30 seconds) to switch between focusing on the content and mind wandering (e.g., skim around the content and not focusing on the content). Additionally or alternatively the subjects may provide discomfort level self-assessments (e.g., categorizing current discomfort as none, slight, moderate, intense, etc.) at various points during a data gathering experience. Self reported discomfort levels may be correlated with image, audio, or other sensor data to identify training data from which relationships between physiological data and perception of discomfort may be determined or learned, e.g., via neural network training processes.

In some implementations, one or more pupillary or EEG characteristics may be determined, aggregated, and used to classify the user's attentive state and/or discomfort using statistical or machine learning techniques. In some implementations, the physiological data is classified based on comparing the variability of the physiological data to a threshold. For example, if the baseline for a user's EEG data is determined during an initial segment of time (e.g., 30-60 seconds), and during a subsequent segment of time following an auditory stimulus (e.g., 5 seconds) the EEG data deviates more than +/−10% from the EEG baseline during the subsequent segment of time, than the techniques described herein could classify the user as transitioned away from the first attentive state (e.g., learning by focusing on a relevant area of the content, such as a teacher) and entered a second attentive state (e.g., mind wandering).

In some implementations, a machine learning model may be used to classify the user's attentive state. For example, labeled training data for a user may be provided to the machine learning model. In some implementations, the machine learning model is a neural network (e.g., an artificial neural network), decision tree, support vector machine, Bayesian network, or the like. These labels may be collected from the user beforehand, or from a population of people beforehand, and fine-tuned later on individual users.

At block 506, the method 500 further determines a modification to the content based on the attentive state and/or current discomfort of the user and presents the modified content to the user. Various types of modifications may be used to stimulate/renew attention to the content and thus mitigate perception of discomfort. For example, a modification may stimulate user attention to the content by changing the content, initiating a new type of experience, moving the content within the XR environment, enlarging the content, increasing a volume of the content, increasing a contrast or brightness of the content, and/or extending the time period during which the content is provided. In some implementations, content is adjusted based on the attentive state, e.g., based on the level of attentiveness to content, attentiveness to discomfort, or relative attention being paid to the content or discomfort.

In some implementations the content is modified to provide a view or other sensory experience the user's self that reduces or eliminates reminders of a source of discomfort in the user's visual or auditory senses. For example, a user experiencing discomfort associated with a missing arm may see a virtual arm in place of the missing arm in an XR environment in which the user sees a representation of himself, e.g., the missing arm may be simulated using a relatively realistic mirror image of the user's remaining arm. In another example, a user with a burn injury may see content that simulates the appearance of the user's skin without the burn. In another example, scars are virtually erased in the content provided to the user.

In some implementations, the modified content provides a visualization to help a user disassociate with discomfort. In some implementations, the modified content provides a meditation experience to help the user focus on something specific (e.g., breath). In some implementations, the modified content encourages a user to unlearn learned discomfort, for example, by providing real-time feedback about stress (associated with actual discomfort) that encourages a user to understand and identify periods of time where perceived discomfort does not correspond to actual discomfort being experienced.

In some implementations, the method 500 determines determining a level of perception of discomfort by the user based on the physiological data, where the level of perception of discomfort provides a specific type of attentive state information. For example, a machine learning model may be trained based on training data in which users provide discomfort level assessments as physiological data is tracked so that the machine learning model can predict level of attention to content, level of attention to discomfort, and a level of perception of discomfort based on physiological data. A determined level of perception of discomfort during the presentation of content may be used to adjusts an amount of a distracting stimulation in the content, e.g., more perceived discomfort may be used to determine to provide more stimulus and vice versa.

In some implementations, the method 500 provides feedback to a second user, the feedback corresponding to the level of perception of discomfort by the user. For example, feedback may be provided to the user's physician, surgeon, dentist, therapist, or other professional service provider to facilitate care, treatment, and/or other services. In one example, during a physical therapy session, the therapist receives feedback about the user's perception of or attention to discomfort during a physical therapy session in order to optimize the activities during the session to best server the user. For example, during a therapy session, a range of motion and the attentive state of a user may be tracked and used to enhance the session. For example, the tracking may be used to generate a correlation between range of motion (e.g., different values/ranges corresponding to the angles and other physical relationships amongst the user's body parts that correspond to progress) and discomfort during physical therapy experience.

In some implementations, feedback is provided to a second user during a remote session, for example, in which care, treatment, and/or services are provided by a provider to the user in a multi-user 3D environment, e.g., in a communication session in which one or more elements of an XR environment are shared amongst the multiple users.

In some implementations, method 500 provides feedback to the user (and/or another person) about a possible source or trigger associated with the perception of discomfort. For example, certain content, environments, user postures, user activities (e.g., sedentary, active, running, swimming, jumping, etc.), user states (e.g., standing, siting, laying, hot, sweating, cold, shivering, etc.), times of day, times of the week, times of the year, or other circumstances may be identified as being associated with a user's attentive state changing to focus more on a discomfort (e.g., an less on provided content). User attention to discomfort may be based on where the user is looking relative to real world or virtual content and thus may be used to determine a source of discomfort, e.g., which portion of the user's body is experiencing discomfort to which the user is currently paying attention. For example, the user's attention may be directed to a particular portion of the user's body (e.g., the user may look at his or her injured wrist when the perception of discomfort in that wrist is elevated) when the user experiences new or increased discomfort in that portion of his or her body. Tracking physiological data may accordingly be used to identify one or more potential sources and/or triggers associated with the perception of discomfort. In some implementations, the method 500 predicts a source and/or trigger of the discomfort based on the physiological data and provides content modification and/or feedback based on the predicted source of the discomfort.

In some implementations, the attention of a user is influenced by presenting content during an experience to distract the user from unpleasant precepts. The techniques may be used to help a user prepare for a surgical procedure. This may reduce pre-operative anxiety, which may correlate with reduce post-operative discomfort. It may decrease the need for and/or use of discomfort reducing medications, and ultimately lower risks associated with developing dependence upon opioids and other discomfort medications. It may also enable patients to be ambulatory sooner after a surgical procedure. It may help patients resolve fears of certain medical techniques and procedures, e.g., needle-phobia. The techniques disclosed herein may be used to help users with acute or chronic discomfort.

Figure 6:
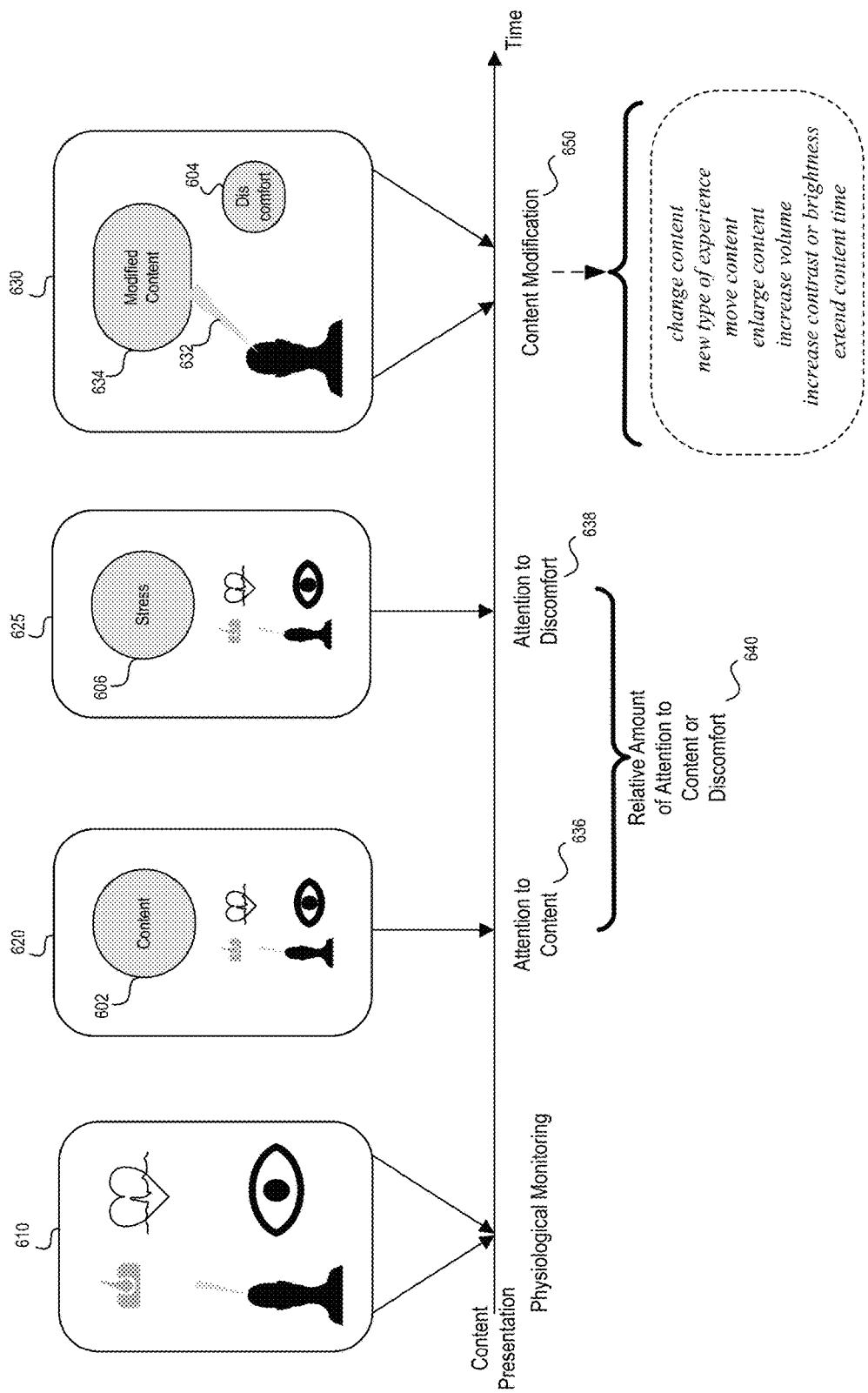
FIG. 6 illustrates another example of assessing an attentive state of the user viewing content based on physiological data in accordance with some implementations.

FIG. 6 illustrates modifying content based on assessing an attentive state of the user viewing the content based on physiological data. In this example physiological monitoring begins at block 610. At block 620, content 602 is presented and physiological data is obtained and used to determine or assess attention to content 636. At block 625, the user's stress 606 is assessed based on the obtained physiological data and used to determine or asses attention to discomfort 638. The relative amount of attention being paid to the content and discomfort 640 is determined based on the attention to content 636 and the attention to discomfort 638. At block 630, the relative amount of attention being paid to the content and discomfort 640 is used to determine modified content 634, e.g., by determining a content modification 650. For example, the modified content 634 may be configured to encourage the user to pay relatively more attention to the modified content 634 and less attention to the discomfort 604.

To determine stress, the user's physiologic data such as eye gaze characteristic data, pupillary data, electrodermal (EDA) data, and heart rate data may be monitored for changes relative to baseline values. Stress may also be determined based on assessing context, e.g., aspects of the content being presented, and/or any other aspects of the user's environment. For example, determining context data may involve using computer vision to generate a scene understanding of the visual and/or auditory attributes of the physical environment, such as where is the user, what is the user doing, what objects are nearby. Additionally, or alternatively, determining context data of the experience may involve determining a scene understanding of the visual and/or auditory attributes of the content presentation. For example, the content and environment may include one or more people, objects, or other background objects that are within view of the user that may be detected by an objection detection algorithm, face detection algorithm, or the like. Stress may be determined by analyzing the user's physiological data and the context data of the content and/or environment. This may involve identifying when the user is exhibiting a high stress level (e.g., a "distress" level) or a reasonable level of stress (e.g., a "eustress" level).

Figure 7:
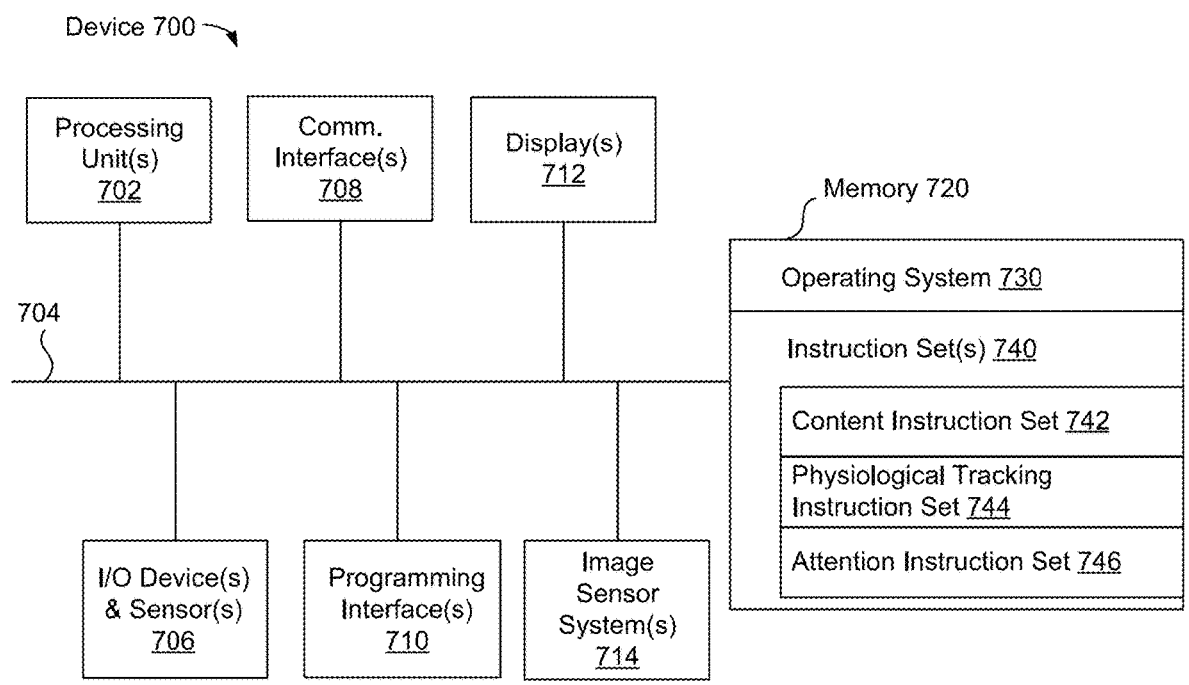
FIG. 7 illustrates device components of an exemplary device in accordance with some implementations.

FIG. 7 is a block diagram of an example device 700. Device 700 illustrates an exemplary device configuration for device 10. While certain specific features are illustrated, those skilled in the art will appreciate from the present disclosure that various other features have not been illustrated for the sake of brevity, and so as not to obscure more pertinent aspects of the implementations disclosed herein. To that end, as a non-limiting example, in some implementations the device 10 includes one or more processing units 702 (e.g., microprocessors, ASICs, FPGAs, GPUs, CPUs, processing cores, and/or the like), one or more input/output (I/O) devices and sensors 706, one or more communication interfaces 708 (e.g., USB, FIREWIRE, THUNDERBOLT, IEEE 802.3x, IEEE 802.11x, IEEE 802.16x, GSM, CDMA, TDMA, GPS, IR, BLUETOOTH, ZIGBEE, SPI, I2C, and/or the like type interface), one or more programming (e.g., I/O) interfaces 710, one or more displays 712, one or more interior and/or exterior facing image sensor systems 714, a memory 720, and one or more communication buses 704 for interconnecting these and various other components.

In some implementations, the one or more communication buses 704 include circuitry that interconnects and controls communications between system components. In some implementations, the one or more I/O devices and sensors 706 include at least one of an inertial measurement unit (IMU), an accelerometer, a magnetometer, a gyroscope, a thermometer, one or more physiological sensors (e.g., blood pressure monitor, heart rate monitor, blood oxygen sensor, blood glucose sensor, etc.), one or more microphones, one or more speakers, a haptics engine, one or more depth sensors (e.g., a structured light, a time-of-flight, or the like), and/or the like.

In some implementations, the one or more displays 712 are configured to present a view of a physical environment or a graphical environment to the user. In some implementations, the one or more displays 712 correspond to holographic, digital light processing (DLP), liquid-crystal display (LCD), liquid-crystal on silicon (LCoS), organic light-emitting field-effect transitory (OLET), organic light-emitting diode (OLED), surface-conduction electron-emitter display (SED), field-emission display (FED), quantum-dot light-emitting diode (QD-LED), micro-electromechanical system (MEMS), and/or the like display types. In some implementations, the one or more displays 712 correspond to diffractive, reflective, polarized, holographic, etc. waveguide displays. In one example, the device 10 includes a single display. In another example, the device 10 includes a display for each eye of the user.

In some implementations, the one or more image sensor systems 714 are configured to obtain image data that corresponds to at least a portion of the physical environment 5. For example, the one or more image sensor systems 714 include one or more RGB cameras (e.g., with a complimentary metal-oxide-semiconductor (CMOS) image sensor or a charge-coupled device (CCD) image sensor), monochrome cameras, IR cameras, depth cameras, event-based cameras, and/or the like. In various implementations, the one or more image sensor systems 714 further include illumination sources that emit light, such as a flash. In various implementations, the one or more image sensor systems 714 further include an on-camera image signal processor (ISP) configured to execute a plurality of processing operations on the image data.

The memory 720 includes high-speed random-access memory, such as DRAM, SRAM, DDR RAM, or other random-access solid-state memory devices. In some implementations, the memory 720 includes non-volatile memory, such as one or more magnetic disk storage devices, optical disk storage devices, flash memory devices, or other non-volatile solid-state storage devices. The memory 720 optionally includes one or more storage devices remotely located from the one or more processing units 702. The memory 720 includes a non-transitory computer readable storage medium.

In some implementations, the memory 720 or the non-transitory computer readable storage medium of the memory 720 stores an optional operating system 730 and one or more instruction set(s) 740. The operating system 730 includes procedures for handling various basic system services and for performing hardware dependent tasks. In some implementations, the instruction set(s) 740 include executable software defined by binary information stored in the form of electrical charge. In some implementations, the instruction set(s) 740 are software that is executable by the one or more processing units 702 to carry out one or more of the techniques described herein.

The instruction set(s) 740 include a content instruction set 742, a physiological tracking instruction set 744, an attention instruction set 746, and a modification instruction set 748. The instruction set(s) 740 may be embodied a single software executable or multiple software executables.

In some implementations, the content instruction set 742 is executable by the processing unit(s) 702 to provide and/or track content for display on or presentation via a device. The content instruction set 742 may be configured to monitor and track the content over time (e.g., during an experience). In some implementations, the content instruction set 742 may be configured to inject modifications into content using one or more of the techniques discussed herein or as otherwise may be appropriate. To these ends, in various implementations, the instruction includes instructions and/or logic therefor, and heuristics and metadata therefor.

In some implementations, the physiological tracking instruction set 744 is executable by the processing unit(s) 702 to track a user's physiological attributes (e.g., characteristics of a user's eyes, skin, brainwaves, motion, heartrate, temperature, etc.) using one or more of the techniques discussed herein or as otherwise may be appropriate. To these ends, in various implementations, the instruction includes instructions and/or logic therefor, and heuristics and metadata therefor.

In some implementations, the attention instruction set 746 is executable by the processing unit(s) 702 to determine an attentive state of a user based on the user's physiological attributes using one or more of the techniques discussed herein or as otherwise may be appropriate. To these ends, in various implementations, the instruction includes instructions and/or logic therefor, and heuristics and metadata therefor.

Although the instruction set(s) 740 are shown as residing on a single device, it should be understood that in other implementations, any combination of the elements may be located in separate computing devices. Moreover, FIG. 7 is intended more as functional description of the various features which are present in a particular implementation as opposed to a structural schematic of the implementations described herein. As recognized by those of ordinary skill in the art, items shown separately could be combined and some items could be separated. The actual number of instructions sets and how features are allocated among them may vary from one implementation to another and may depend in part on the particular combination of hardware, software, and/or firmware chosen for a particular implementation.

Figure 8:
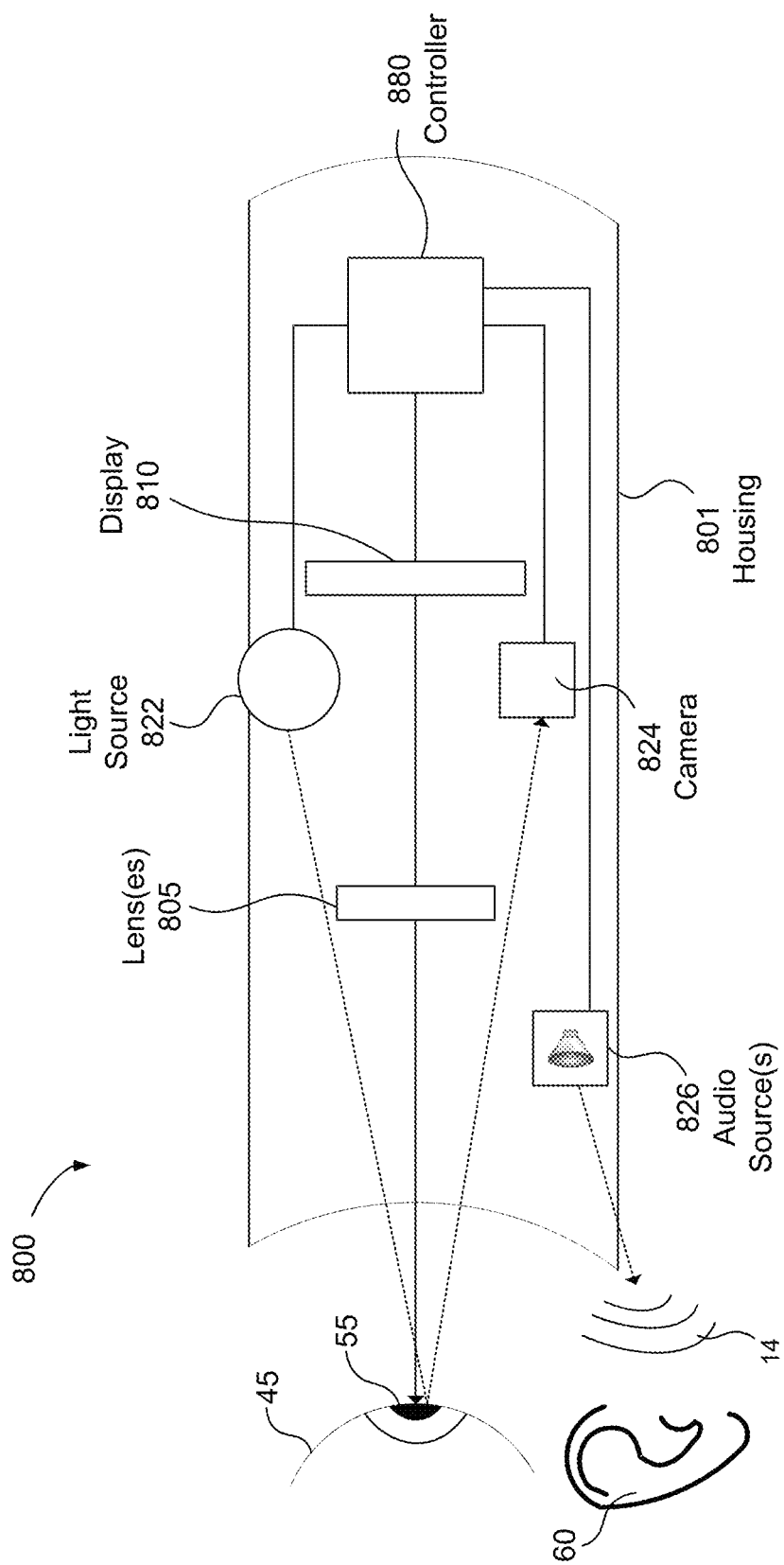
FIG. 8 illustrates an example head-mounted device (HMD) in accordance with some implementations.

FIG. 8 illustrates a block diagram of an exemplary head-mounted device 800 in accordance with some implementations. The head-mounted device 800 includes a housing 801 (or enclosure) that houses various components of the head-mounted device 800. The housing 801 includes (or is coupled to) an eye pad (not shown) disposed at a proximal (to the user 25) end of the housing 801. In various implementations, the eye pad is a plastic or rubber piece that comfortably and snugly keeps the head-mounted device 800 in the proper position on the face of the user 25 (e.g., surrounding the eye of the user 25).

The housing 801 houses a display 810 that displays an image, emitting light towards or onto the eye of a user 25. In various implementations, the display 810 emits the light through an eyepiece having one or more lenses 805 that refracts the light emitted by the display 810, making the display appear to the user 25 to be at a virtual distance farther than the actual distance from the eye to the display 810. For the user 25 to be able to focus on the display 810, in various implementations, the virtual distance is at least greater than a minimum focal distance of the eye (e.g., 8 cm). Further, in order to provide a better user experience, in various implementations, the virtual distance is greater than 1 meter.

The housing 801 also houses a tracking system including one or more light sources 822, camera 824, and a controller 880. The one or more light sources 822 emit light onto the eye of the user 25 that reflects as a light pattern (e.g., a circle of glints) that can be detected by the camera 824. Based on the light pattern, the controller 880 can determine an eye tracking characteristic of the user 25. For example, the controller 880 can determine a gaze direction and/or a blinking state (eyes open or eyes closed) of the user 25. As another example, the controller 880 can determine a pupil center, a pupil size, or a point of regard. Thus, in various implementations, the light is emitted by the one or more light sources 822, reflects off the eye of the user 25, and is detected by the camera 824. In various implementations, the light from the eye of the user 25 is reflected off a hot mirror or passed through an eyepiece before reaching the camera 824.

The housing 801 also houses an audio system that includes one or more audio source(s) 826 that the controller can utilize for providing audio to the user ears 60 via sound waves 14 per the techniques described herein. For example, audio source(s) 826 can provide sound for both background sound and the content that can be presented spatially in a 3D coordinate system. The audio source(s) 826 can include a speaker, a connection to an external speaker system such as headphones, or an external speaker connected via a wireless connection.

The display 810 emits light in a first wavelength range and the one or more light sources 822 emit light in a second wavelength range. Similarly, the camera 824 detects light in the second wavelength range. In various implementations, the first wavelength range is a visible wavelength range (e.g., a wavelength range within the visible spectrum of approximately 400-700 nm) and the second wavelength range is a near-infrared wavelength range (e.g., a wavelength range within the near-infrared spectrum of approximately 700-1400 nm).

In various implementations, eye tracking (or, in particular, a determined gaze direction) is used to enable user interaction (e.g., the user 25 selects an option on the display 810 by looking at it), provide foveated rendering (e.g., present a higher resolution in an area of the display 810 the user 25 is looking at and a lower resolution elsewhere on the display 810), correct distortions (e.g., for images to be provided on the display 810), and/or assess the attentive state of the user.

In various implementations, the one or more light sources 822 emit light towards the eye of the user 25 which reflects in the form of a plurality of glints.

In various implementations, the camera 824 is a frame/shutter-based camera that, at a particular point in time or multiple points in time at a frame rate, generates an image of the eye of the user 25. Each image includes a matrix of pixel values corresponding to pixels of the image which correspond to locations of a matrix of light sensors of the camera. In implementations, each image is used to measure or track pupil dilation by measuring a change of the pixel intensities associated with one or both of a user's pupils.

It will be appreciated that the implementations described above are cited by way of example, and that the present invention is not limited to what has been particularly shown and described hereinabove. Rather, the scope includes both combinations of the various features described hereinabove, as well as variations and modifications thereof which would occur to persons skilled in the art upon reading the foregoing description and which are not disclosed in the prior art.

As described above, one aspect of the present technology is the gathering and use of physiological data to improve a user's experience. The present disclosure contemplates that in some instances, this gathered data may include personal information data that uniquely identifies a specific person or can be used to identify interests, traits, or tendencies of a specific person. Such personal information data can include physiological data, demographic data, location-based data, telephone numbers, email addresses, home addresses, device characteristics of personal devices, or any other personal information.

The present disclosure recognizes that the use of such personal information data, in the present technology, can be used to the benefit of users. For example, the personal information data can be used to provide information to a medical provider assisting the user. Accordingly, use of such personal information data enables calculated control of the electronic device. Further, other uses for personal information data that benefit the user are also contemplated by the present disclosure.

The present disclosure further contemplates that the entities responsible for the collection, analysis, disclosure, transfer, storage, or other use of such personal information and/or physiological data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates implementations in which users selectively block the use of, or access to, personal information data. That is, the present disclosure contemplates that hardware or software elements can be provided to prevent or block access to such personal information data. For example, in the case of user-tailored content delivery services, the present technology can be configured to allow users to select to "opt in" or "opt out" of participation in the collection of personal information data during registration for services. In another example, users can select not to provide personal information data for targeted content delivery services. In yet another example, users can select to not provide personal information, but permit the transfer of anonymous information for the purpose of improving the functioning of the device.

Therefore, although the present disclosure broadly covers use of personal information data to implement one or more various disclosed implementations, the present disclosure also contemplates that the various implementations can also be implemented without the need for accessing such personal information data. That is, the various embodiments of the present technology are not rendered inoperable due to the lack of all or a portion of such personal information data. For example, content can be selected and delivered to users by inferring preferences or settings based on non-personal information data or a bare minimum amount of personal information, such as the content being requested by the device associated with a user, other non-personal information available to the content delivery services, or publicly available information.

In some embodiments, data is stored using a public/private key system that only allows the owner of the data to decrypt the stored data. In some other implementations, the data may be stored anonymously (e.g., without identifying and/or personal information about the user, such as a legal name, username, time and location data, or the like). In this way, other users, hackers, or third parties cannot determine the identity of the user associated with the stored data. In some implementations, a user may access his or her stored data from a user device that is different than the one used to upload the stored data. In these instances, the user may be required to provide login credentials to access their stored data.

Numerous specific details are set forth herein to provide a thorough understanding of the claimed subject matter. Those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing the terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general-purpose computing apparatus to a specialized computing apparatus implementing one or more implementations of the present subject matter. Any suitable programming, scripting, or other type of language or combinations of languages may be used to implement the teachings contained herein in software to be used in programming or configuring a computing device.

Implementations of the methods disclosed herein may be performed in the operation of such computing devices. The order of the blocks presented in the examples above can be varied for example, blocks can be re-ordered, combined, or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or value beyond those recited. Headings, lists, and numbering included herein are for ease of explanation only and are not meant to be limiting.

It will also be understood that, although the terms "first," "second," etc. may be used herein to describe various objects, these objects should not be limited by these terms. These terms are only used to distinguish one object from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "or" as used herein refers to and encompasses any and all possible combinations of one or more of the associated listed items. It will be further understood that the terms "comprises" or "comprising," when used in this specification, specify the presence of stated features, integers, steps, operations, objects, or components, but do not preclude the presence or addition of one or more other features, integers, steps, operations, objects, components, or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description and summary of the invention are to be understood as being in every respect illustrative and exemplary, but not restrictive, and the scope of the invention disclosed herein is not to be determined only from the detailed description of illustrative implementations but according to the full breadth permitted by patent laws. It is to be understood that the implementations shown and described herein are only illustrative of the principles of the present invention and that various modification may be implemented by those skilled in the art without departing from the scope and spirit of the invention.

What is claimed is:

1. A method comprising:
   at a device comprising a processor:
   presenting content to a user in an extended reality (XR) environment and obtaining physiological data associated with the user via one or more physiological sensors;
   determining an attentive state of the user based on the physiological data, wherein the attentive state of the user is associated with whether attention of the user is directed to the content or discomfort and is determined based on identifying, within a time period, an attention shift and a discomfort response indicating that the attention shift is based on the discomfort rather than another trigger, wherein the discomfort is due to an injury or condition of the user existing prior to presenting the content to the user in the XR environment;
   determining a modification to the content based on the attentive state of the user; and
   presenting the modified content to the user.

2. The method of claim 1, wherein the attentive state is further determined based on assessing attention to the discomfort based on tracking stress of the user based on the physiological data.

3. The method of claim 2, wherein stress is tracked based on heart rate, respiration rate, eye characteristics, body temperature, or EEG pattern identified based on the physiological data.

4. The method of claim 1, wherein the modification stimulates user attention to the content by:
   changing the content;
   initiating a new type of experience;
   moving the content within the XR environment;
   enlarging the content;
   increasing a volume of the content;
   increasing a contrast or brightness of the content; or
   extending the time period during which the content is provided.

5. The method of claim 1, wherein attentive state is determined based on using the physiological data to measure gaze or body stability.

6. The method of claim 1, wherein attentive state is determined based on identifying a facial expression or facial gesture.

7. The method of claim 1, wherein attentive state is determined based on determining a level of attentiveness to the content.

8. The method of claim 1, wherein the attentive state is determined based on tracking gaze direction to track when the user is gazing at the content.

9. The method of claim 1, further comprising determining a level of perception of discomfort by the user based on the attentive state.

10. The method of claim 9, further comprising adjusting an amount of a distracting stimulation in the content based on the level of perception of discomfort.

11. The method of claim 9, further comprising providing feedback to a second user, the feedback corresponding to the level of perception of discomfort by the user.

12. The method of claim 11, wherein the feedback is provided within a view of the XR environment provided to the second user.

13. The method of claim 1, wherein determining the attentive state comprises using an attention map to track user focus, wherein the attention map identifies a relevant area and a non-relevant area.

14. The method of claim 13 further comprising determining to what a user is paying attention based on the attention map.

15. The method of claim 13, wherein the attentive state is determined based on assessing transitions based on the attention map.

16. The method of claim 1 further comprising:
   tracking a range of motion and the attentive state during a physical therapy experience;
   generating a correlation between range of motion and discomfort during physical therapy experience based on the tracking.

17. The method of claim 1 further comprising:
   predicting a source of the discomfort based on the physiological data; and
   providing feedback based on the predicted source of the discomfort.

18. The method of claim 1, wherein determining the attentive state of the user is based on:
   determining that the user is not attentive to the content by using gaze data of the physiological data to determine that a gaze of a user is not focused on relevant portions of the content; and
   determining that the user is attentive to the discomfort by using physiological data to detect the discomfort response.

19. The method of claim 1, wherein determining the attentive state of the user is based on:
   determining that the user is not attentive to the content by using gaze data of the physiological data to determine that a gaze of a user is not focused on relevant portions of the content; and
   determining that the user is attentive to the discomfort by using physiological data to detect a stress response.

20. The method of claim 19, wherein the stress response is detected based on tracking heart rate, respiration rate, body temperature, EEG pattern, or facial gesture.

21. The method of claim 1 further comprising determining a source of the discomfort, wherein the modification alters an appearance associated with a portion of a body of the user to reduce a reminder of the source of the discomfort in the visual senses of the user; and the portion of the body is a missing limb and the appearance associated with the portion of the body is altered to reduce the reminder of the source of the discomfort by displaying a virtual limb in place of the missing limb.

22. The method of claim 21, wherein the missing limb is simulated based on an image of an opposing limb of the user.

23. The method of claim 1 further comprising determining a source of the discomfort, wherein the modification alters an appearance associated with a portion of a body of the user to reduce a reminder of the source of the discomfort in the visual senses of the user; and the portion of the body is skin, the source of the discomfort is associated with a scar on the skin, and the appearance associated with the portion of the body is altered to reduce the reminder of the source of the discomfort by erasing the appearance of the scar on the skin.

24. The method of claim 1 further comprising determining a source of the discomfort, wherein the modification alters an appearance associated with a portion of a body of the user to reduce a reminder of the source of the discomfort in the visual senses of the user; and the portion of the body is skin, the source of the discomfort is a burn on the skin, and the appearance associated with the portion of the body is altered to reduce the reminder of the source of the discomfort by simulating the appearance of the skin without the burn.

25. The method of claim 1, wherein identifying the discomfort response comprises identifying a user action associated with a location of the discomfort on the user.

26. The method of claim 1, wherein the discomfort response is identified based on identifying a user action comprising rubbing, massaging, squeezing, or touching a body part associated with the discomfort.

27. The method of claim 1, wherein the discomfort response is identified based on identifying a user action comprising moving a body part associated with the discomfort.

28. The method of claim 1, wherein the discomfort response is identified based on identifying a user action comprising gazing at a body part associated with the discomfort.

29. A device comprising:

a non-transitory computer-readable storage medium; and one or more processors coupled to the non-transitory computer-readable storage medium, wherein the non-transitory computer-readable storage medium comprises program instructions that, when executed on the one or more processors, cause the system to perform operations comprising:

presenting content to a user in an extended reality (XR) environment and obtaining physiological data associated with the user via one or more physiological sensors;

determining an attentive state of the user based on the physiological data, wherein the attentive state of the user is associated with whether attention of the user is directed to the content or discomfort and is determined based on identifying, within a time period, an attention shift and a discomfort response indicating that the attention shift is based on the discomfort rather than another trigger, wherein the discomfort is due to an injury or condition of the user existing prior to presenting the content to the user in the XR environment;

determining a modification to the content based on the attentive state of the user; and presenting the modified content to the user.

30. The device of claim 29, wherein the attentive state is further determined based on assessing attention to the discomfort based on tracking stress of the user based on the physiological data.

31. A non-transitory computer-readable storage medium, storing instructions executable via one or more processors to perform operations comprising:

presenting content to a user in an extended reality (XR) environment and obtaining physiological data associated with the user via one or more physiological sensors;

determining an attentive state of the user based on the physiological data, wherein the attentive state of the user is associated with whether attention of the user is directed to the content or discomfort and is determined based on identifying, within a time period, an attention shift and a discomfort response indicating that the attention shift is based on the discomfort rather than another trigger, wherein the discomfort is due to an injury or condition of the user existing prior to presenting the content to the user in the XR environment;

determining a modification to the content based on the attentive state of the user; and presenting the modified content to the user.

* * * * *

UNITED STATES PATENT AND TRADEMARK OFFICE
CERTIFICATE OF CORRECTION

| | | |
|---|---|---|
| PATENT NO. | : 12,099,654 B1 | Page 1 of 1 |
| APPLICATION NO. | : 17/838441 | |
| DATED | : September 24, 2024 | |
| INVENTOR(S) | : Grant H. Mulliken et al. | |

It is certified that error appears in the above-identified patent and that said Letters Patent is hereby corrected as shown below:

On the Title Page

ABSTRACT, Item (57), Line 9, reads:
"... the user's stress is also assessed and used an ..."
Should read:
--... the user's stress is also assessed and used as an ...--

Signed and Sealed this
Twenty-second Day of October, 2024

Katherine Kelly Vidal
*Director of the United States Patent and Trademark Office*